(12) United States Patent
Balczewski et al.

(10) Patent No.: US 11,523,746 B2
(45) Date of Patent: Dec. 13, 2022

(54) IMPLANTABLE MEDICAL DEVICE HAVING TWO ELECTRODES IN THE HEADER

(71) Applicant: Cardiac Pacemakers, Inc., St. Paul, MN (US)

(72) Inventors: Ron A. Balczewski, Bloomington, MN (US); Jean M. Bobgan, Maple Grove, MN (US); Aleksandra Kharam, Maple Grove, MN (US); David P. Stieper, North Branch, MN (US); Scott R. Vanderlinde, Plymouth, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 425 days.

(21) Appl. No.: 16/666,050

(22) Filed: Oct. 28, 2019

(65) Prior Publication Data
US 2020/0129088 A1   Apr. 30, 2020

Related U.S. Application Data

(60) Provisional application No. 62/751,677, filed on Oct. 28, 2018.

(51) Int. Cl.
*A61B 5/0538* (2021.01)
*A61B 5/00* (2006.01)

(52) U.S. Cl.
CPC ............ *A61B 5/0538* (2013.01); *A61B 5/686* (2013.01); *A61B 2560/045* (2013.01); *A61B 2560/0418* (2013.01); *A61B 2560/0468* (2013.01); *A61B 2562/043* (2013.01)

(58) Field of Classification Search
CPC ..... A61B 5/0538; A61B 5/0809; A61B 5/085; A61B 5/686; A61B 2560/0418; A61B 2560/045; A61B 2560/0468; A61B 2560/043; A61N 1/36521; A61N 1/3752; A61N 1/3756
See application file for complete search history.

(56) References Cited

U.S. PATENT DOCUMENTS

| 5,217,010 A | 6/1993 | Tsitlik et al. |
| 5,643,328 A | 7/1997 | Cooke et al. |
| 5,929,825 A | 7/1999 | Niu et al. |

(Continued)

FOREIGN PATENT DOCUMENTS

| CN | 101094606 A | 12/2007 |
| CN | 103298522 A | 9/2013 |

(Continued)

OTHER PUBLICATIONS

International Search Report and Written Opinion issued in PCT/US2019/058362, dated Feb. 21, 2020, 12 pages.

(Continued)

*Primary Examiner* — Sean P Dougherty
*Assistant Examiner* — Alexander H Connor
(74) *Attorney, Agent, or Firm* — Faegre Drinker Biddle & Reath LLP

(57) ABSTRACT

Various aspects of the present disclosure are directed toward apparatuses, systems, and methods for supporting components of an implantable medical device. The apparatuses, systems, and methods may include a first electrode and a second electrode and a scaffold assembly configured to support the first electrode and the second electrode.

15 Claims, 4 Drawing Sheets

(56) References Cited

U.S. PATENT DOCUMENTS

| | | |
|---|---|---|
| 6,456,256 B1 | 9/2002 | Amundson et al. |
| 6,804,558 B2 | 10/2004 | Haller et al. |
| 7,319,901 B2 | 1/2008 | Dublin et al. |
| 8,145,324 B1 | 3/2012 | Stevenson et al. |
| 8,843,215 B2 | 9/2014 | Eck et al. |
| 8,989,872 B2 | 3/2015 | Prasannakumar et al. |
| 10,130,820 B2 | 11/2018 | Bobgan et al. |
| 10,237,997 B2 | 3/2019 | Bobgan et al. |
| 10,327,344 B2 | 6/2019 | Bobgan et al. |
| 2005/0134520 A1 | 6/2005 | Rawat et al. |
| 2005/0137480 A1 | 6/2005 | Alt et al. |
| 2005/0245971 A1 | 11/2005 | Brockway et al. |
| 2006/0069322 A1 | 3/2006 | Zhang et al. |
| 2006/0241702 A1 | 10/2006 | Gillberg |
| 2006/0241715 A1 | 10/2006 | Sprain et al. |
| 2006/0247711 A1 | 11/2006 | Verhoef et al. |
| 2006/0247712 A1 | 11/2006 | Fuller et al. |
| 2008/0021522 A1 | 1/2008 | Verhoef et al. |
| 2008/0242976 A1 | 10/2008 | Robertson et al. |
| 2008/0262380 A1 | 10/2008 | Gerber et al. |
| 2008/0262584 A1 | 10/2008 | Bottomley et al. |
| 2008/0269863 A1 | 10/2008 | Alexander et al. |
| 2008/0303728 A1 | 12/2008 | Lee et al. |
| 2009/0248112 A1 | 10/2009 | Mumbru et al. |
| 2010/0168818 A1 | 7/2010 | Barror et al. |
| 2011/0190842 A1 | 8/2011 | Johnson et al. |
| 2012/0001812 A1 | 1/2012 | Zhao et al. |
| 2012/0253340 A1 | 10/2012 | Stevenson et al. |
| 2012/0322317 A1 | 12/2012 | Seeley et al. |
| 2013/0053716 A1 | 2/2013 | Zhang et al. |
| 2013/0150937 A1 | 6/2013 | Kane et al. |
| 2014/0031837 A1 | 1/2014 | Perryman et al. |
| 2014/0135882 A1 | 5/2014 | Prasannakumar et al. |
| 2014/0330346 A1 | 11/2014 | Sharma et al. |
| 2014/0364714 A1 | 12/2014 | Ameri et al. |
| 2015/0094792 A1 | 4/2015 | Kane et al. |
| 2015/0097734 A1 | 4/2015 | Zhao et al. |
| 2015/0224303 A1 | 8/2015 | Tran et al. |
| 2015/0255858 A1 | 9/2015 | Li et al. |
| 2015/0351648 A1 | 12/2015 | Harvey et al. |
| 2016/0114163 A1* | 4/2016 | Franke ................. A61N 1/3756 607/135 |
| 2016/0242667 A1* | 8/2016 | Fay ...................... A61B 5/6859 |
| 2016/0243373 A1 | 8/2016 | Kalgren |
| 2017/0050032 A1 | 2/2017 | Bobgan et al. |
| 2017/0065207 A1 | 3/2017 | Landherr et al. |
| 2017/0296828 A1 | 10/2017 | Bobgan et al. |
| 2017/0303411 A1 | 10/2017 | Bobgan et al. |
| 2017/0303424 A1 | 10/2017 | Bobgan et al. |
| 2017/0354365 A1 | 12/2017 | Zhou |
| 2018/0021570 A1 | 1/2018 | An et al. |
| 2018/0103908 A1 | 4/2018 | Balczewski et al. |
| 2019/0060655 A1 | 2/2019 | Bobgan et al. |
| 2019/0232066 A1* | 8/2019 | Lim .................. A61N 1/37512 |
| 2020/0038101 A1* | 2/2020 | Tobey ................ A61B 18/1206 |
| 2020/0101297 A1* | 4/2020 | Drake ................ A61N 1/36578 |
| 2022/0126104 A1 | 4/2022 | Landherr et al. |
| 2022/0168577 A1 | 6/2022 | Bobgan et al. |

FOREIGN PATENT DOCUMENTS

| | | |
|---|---|---|
| CN | 103381284 A | 11/2013 |
| CN | 103561810 A | 2/2014 |
| CN | 104768610 A | 7/2015 |
| JP | 2016532461 A | 10/2016 |
| WO | 2012/013360 A1 | 2/2012 |

OTHER PUBLICATIONS

International Preliminary Report on Patentability issued in PCT/US2016/047922, dated Mar. 1, 2018, 7 pages.

International Search Report and Written Opinion issued in PCT/US2016/047922, dated Oct. 26, 2016, 10 pages.

* cited by examiner

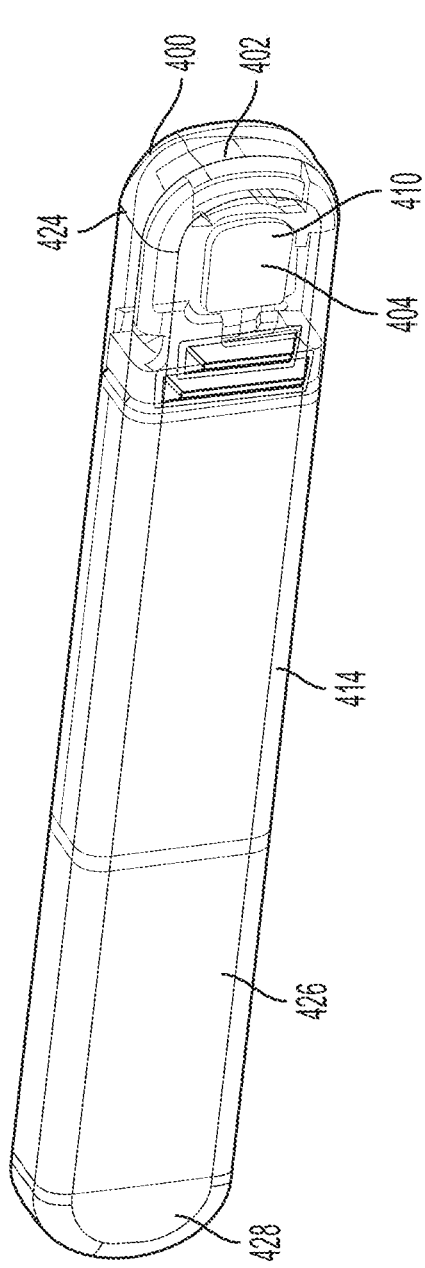
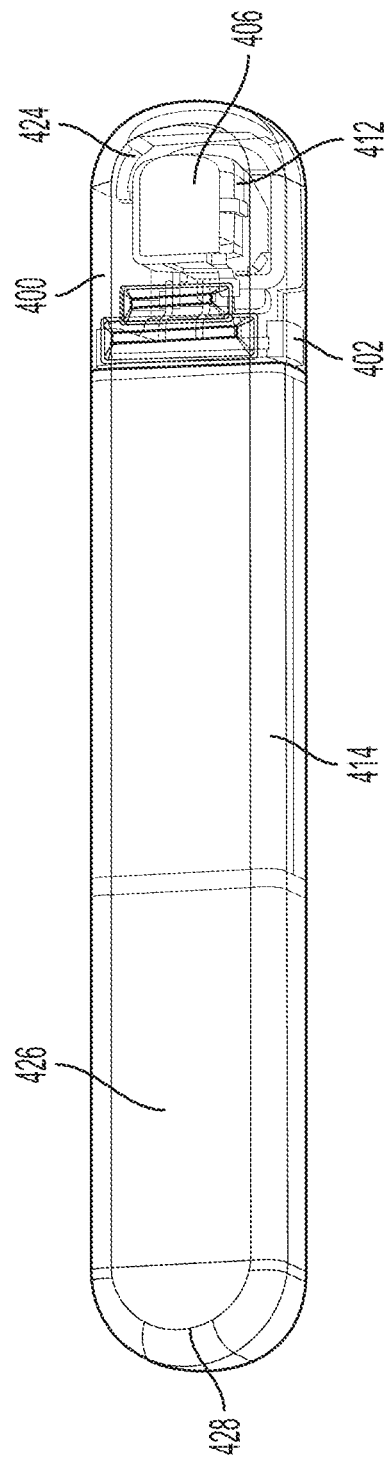
FIG. 4A
FIG. 4B

IMPLANTABLE MEDICAL DEVICE HAVING TWO ELECTRODES IN THE HEADER

CROSS-REFERENCE TO RELATED APPLICATION

This application claims priority to Provisional Application No. 62/751,677, filed Oct. 28, 2018, which is herein incorporated by reference in its entirety.

TECHNICAL FIELD

Embodiments of the present disclosure relate to medical devices and systems for sensing physiological parameters and/or delivering therapy. More specifically, embodiments of the disclosure relate to devices and methods for header core fixation in an implantable medical device.

BACKGROUND

Implantable medical devices (IMDs) may be configured to sense physiological parameters and/or provide therapy and may include one or more electrodes for performing aspects of these functions. IMDs may also include antennas for communicating with other devices. Conventionally, devices such as programmers and wands have been used to cause IMDs to take various actions such as for example, marking recordings of physiological parameters, initiating communications with other devices, and the like.

SUMMARY

In Example 1, an apparatus for supporting components of an implantable medical device includes a first electrode and a second electrode; and a scaffold assembly configured to support and separate the first electrode and the second electrode relative to a longitudinal axis of the scaffold assembly.

In Example 2, further to the apparatus of Example 1, the scaffold assembly is configured to support the first electrode along a first surface of the scaffold assembly and the second electrode along a second surface of the scaffold assembly that opposes the first surface.

In Example 3, further to the apparatus of any one of Examples 1-2, the scaffold assembly is configured to arrange the first electrode parallel to the second electrode.

In Example 4, further to the apparatus of Example 3, the scaffold assembly includes a frontward facing portion and a rearward facing portion, and the first electrode is arranged on the frontward facing portion and the second electrode is arranged on the rearward facing portion.

In Example 5, further to the apparatus of any one of Examples 1-3, the apparatus also includes the implantable medical device having a header, a core assembly including integrated circuitry configured to select between the first electrode and the second electrode.

In Example 6, further to the apparatus of Example 5, the integrated circuitry is configured to measure sensing capability of the first electrode and sensing capability of the second electrode and select between the first electrode and the second electrode in response to determining a greater of the sensing capability of the first electrode and the sensing capability of the second electrode.

In Example 7, further to the apparatus of Example 6, the integrated circuitry is configured to measure impedance on a sensed signal of the first electrode and an impedance on a sensed signal of the second electrode to determine the sensing capability of the first electrode and the sensing capability of the second electrode.

In Example 8, further to the apparatus of any one of Examples 5-7, the first electrode and the second electrode are arranged at a proximal end of the core assembly and further comprising a third electrode arranged at a distal end of the core assembly.

In Example 9, further to the apparatus of Example 8, the integrated circuitry is configured to drive the third electrode and one of the first electrode and the second electrode and to sense another of the first electrode and the second electrode.

In Example 10, further to the apparatus of any one of Examples 5-9, the scaffold assembly is arranged within the header and the scaffold assembly is configured to support and position the first electrode and with a first surface of an interior portion of the header and position the second electrode and with a second surface of the interior portion of the header.

In Example 11, further to the apparatus of any one of Examples 5-10, the integrated circuitry includes a Kelvin connection to the first electrode and the second electrode.

In Example 12, further to the apparatus of any one of Examples 5-11, the apparatus also includes a first electrical connector configured to connect the first electrode to the integrated circuitry within the core assembly and a second electrical connector configured to connect the second electrode to the integrated circuitry within the core assembly.

In Example 13, further to the apparatus of any one of Examples 1-12, the apparatus also includes an antenna arranged on the scaffold and between the first electrode and the second electrode.

In Example 14, further to the apparatus of Example 13, wherein the antenna is arranged along a top portion of the scaffold assembly.

In Example 15, further to the apparatus of any one of Examples 1-14, the first electrode includes a first area and the second electrode includes a second area, and the first area is substantially equal to the first area.

In Example 16, an apparatus for supporting components of an implantable medical device includes a first electrode and a second electrode; and a scaffold assembly configured to interface with a portion of an implantable medical device and configured to support the first electrode along a first surface of the scaffold assembly and the second electrode along a second surface of the scaffold assembly that opposes the first surface.

In Example 17, further to the apparatus of Example 16, the scaffold assembly is configured to arrange the first electrode parallel to the second electrode.

In Example 18, further to the apparatus of Example 17, the scaffold assembly includes a frontward facing portion and a rearward facing portion, and the first electrode is arranged on the frontward facing portion and the second electrode is arranged on the rearward facing portion.

In Example 19, further to the apparatus of Example 16, the apparatus also includes the implantable medical device having a header, a core assembly including integrated circuitry configured to select between the first electrode and the second electrode.

In Example 20, further to the apparatus of Example 19, the integrated circuitry is configured to measure sensing capability of the first electrode and sensing capability of the second electrode and select between the first electrode and the second electrode in response to determining a greater of the sensing capability of the first electrode and the sensing capability of the second electrode.

In Example 21, further to the apparatus of Example 20, the integrated circuitry is configured to measure impedance on a sensed signal of the first electrode and an impedance on a sensed signal of the second electrode to determine the sensing capability of the first electrode and the sensing capability of the second electrode.

In Example 22, further to the apparatus of Example 19, the first electrode and the second electrode are arranged at a proximal end of the core assembly and further comprising a third electrode arranged at a distal end of the core assembly.

In Example 23, further to the apparatus of Example 22, the integrated circuitry is configured to drive the third electrode and one of the first electrode and the second electrode and to sense another of the first electrode and the second electrode.

In Example 24, further to the apparatus of Example 19, the scaffold assembly is arranged within the header and the scaffold assembly is configured to support and position the first electrode and with a first surface of an interior portion of the header and position the second electrode and with a second surface of the interior portion of the header.

In Example 25, further to the apparatus of Example 16, the apparatus also includes an antenna arranged on the scaffold and between the first electrode and the second electrode.

In Example 26, further to the apparatus of Example 19, the first electrode includes a first area and the second electrode includes a second area, and the first area is substantially equal to the first area.

In Example 27, an apparatus includes a medical device configured to be implanted within a body of a patient including: a core assembly having a proximal end and a distal end, a header coupled to the proximal end of the core assembly, a first electrode and a second electrode arranged within the header, a third electrode arranged at the distal end of the core assembly, and a scaffold assembly arranged within the header and configured to support and separate the first electrode and the second electrode relative to a longitudinal axis of the scaffold assembly.

In Example 28, further to the apparatus of Example 27, the scaffold assembly is configured to interface with a portion of the core assembly and configured to support the first electrode along a first surface of the scaffold assembly and the second electrode along a second surface of the scaffold assembly that opposes the first surface.

In Example 29, further to the apparatus of Example 27, the apparatus also includes integrated circuitry arranged within the core assembly and configured to measure sensing capability of the first electrode and sensing capability of the second electrode and select between the first electrode and the second electrode in response to determining a greater of the sensing capability of the first electrode and the sensing capability of the second electrode.

In Example 30, further to the apparatus of Example 29, the integrated circuitry is configured to measure impedance on a sensed signal of the first electrode and an impedance on a sensed signal of the second electrode to determine the sensing capability of the first electrode and the sensing capability of the second electrode.

In Example 31, further to the apparatus of Example 29, the integrated circuitry is configured to drive the third electrode and one of the first electrode and the second electrode and to sense another of the first electrode and the second electrode.

In Example 32, further to the apparatus of Example 29, the scaffold assembly is arranged within the header and the scaffold assembly is configured to support and position the first electrode and with a first surface of an interior portion of the header and position the second electrode and with a second surface of the interior portion of the header.

In Example 33, a method includes interfacing a scaffold assembly with a core assembly of an implantable medical device; arranging a first circuit component and a second circuit component on portions of the scaffold assembly, the scaffold assembly being configured to position and support the first circuit component relative to the second circuit component; and arranging a header assembly over and around the scaffold assembly and interfacing the header assembly with the core assembly.

In Example 34, further to the method of Example 33, the method also includes electrically connecting the first circuit component and the second circuit component to an integrated circuit arranged within the core assembly.

In Example 35, further to the method of Example 34, electrically connecting the first circuit component and the second circuit component comprises welding the first circuit component and the second circuit to respective electrical connectors coupled to the integrated circuit.

While multiple embodiments are disclosed, still other embodiments of the present disclosure will become apparent to those skilled in the art from the following detailed description, which shows and describes illustrative embodiments of the subject matter disclosed herein. Accordingly, the drawings and detailed description are to be regarded as illustrative in nature and not restrictive.

BRIEF DESCRIPTION OF THE DRAWINGS

FIG. 4A is a front-facing view of an IMD.

FIG. 4B is a back-facing view of the IMD shown in FIG. 4A.

Figure 1:
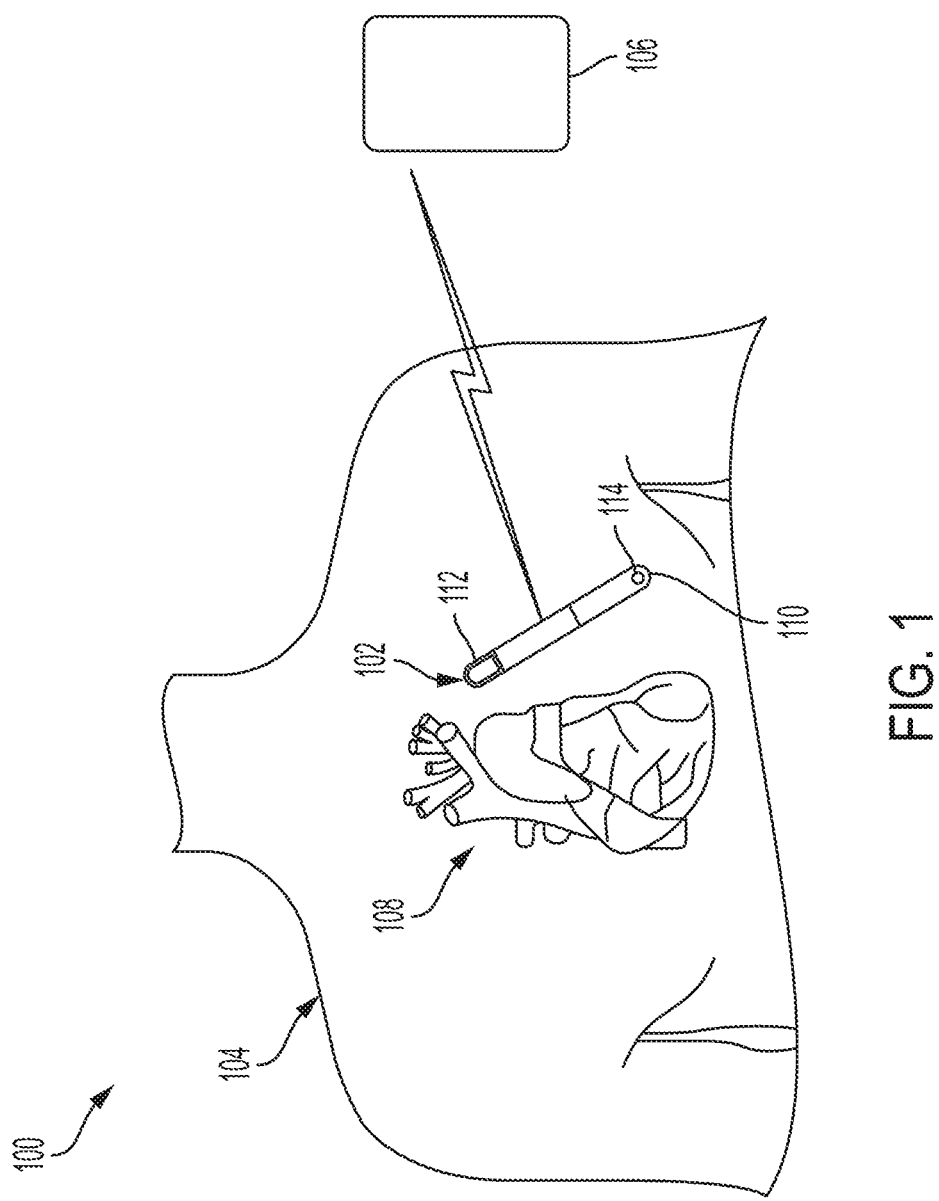
FIG. 1 is a schematic illustration of a system having an implantable medical device (IMD) and a receiving device.

While the subject matter disclosed herein is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the subject matter disclosed herein as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

FIG. 1 is a schematic illustration of a system 100 including an implantable medical device (IMD) 102 implanted within a patient's body 104 and configured to communicate with a receiving device 106. In embodiments, the IMD 102 may be implanted subcutaneously within an implantation location or pocket in the patient's chest or abdomen and may be configured to monitor (e.g., sense and/or record) physiological parameters associated with the patient's heart 108. In embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac activation signals, heart sounds, blood pressure measurements, oxygen saturations, and/or the like.

In certain instances, the IMD 102 may be configured to monitor physiological parameters that may include one or more signals indicative of a patient's physical activity level and/or metabolic level, such as an acceleration signal. In certain instances, the IMD 102 may be configured to monitor physiological parameters associated with one or more other organs, systems, and/or the like. The IMD 102 may be configured to sense and/or record at regular intervals, continuously, and/or in response to a detected event. In certain instances, such a detected event may be detected by one or more sensors of the IMD 102, another IMD (not shown), an external device (e.g., the receiving device 106), and/or the like. In addition, the IMD 102 may be configured to detect a variety of physiological signals that may be used in connection with various diagnostic, therapeutic, and/or monitoring implementations. For example, the IMD 102 may include sensors or circuitry for detecting respiratory system signals, cardiac system signals, and/or signals related to patient activity. In certain instances, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

For purposes of illustration, and not of limitation, various embodiments of devices that may be used to record physiological parameters in accordance with the present disclosure are described herein in the context of IMDs that may be implanted under the skin in the chest region of a patient.

As shown, the IMD 102 may include a housing 110 having two electrodes 112 and 114 coupled thereto. According to certain instances, the IMD 102 may include any number of electrodes (and/or other types of sensors such as, e.g., thermometers, barometers, pressure sensors, optical sensors, motion sensors, and/or the like) in any number of various types of configurations, and the housing 110 may include any number of different shapes, sizes, and/or features. In certain instances, the IMD 102 may be configured to sense physiological parameters and record the physiological parameters. For example, the IMD 102 may be configured to activate (e.g., periodically, continuously, upon detection of an event, and/or the like), record a specified amount of data (e.g., physiological parameters) in a memory, and communicate that recorded data to a receiving device 106. In the case of an IDM, for example, the IMD 102 may activate, record cardiac signals for a certain period of time, deactivate, and activate to communicate the recorded signals to the receiving device 106.

In various instances, the receiving device 106 may be, for example, a programmer, controller, patient monitoring system, and/or the like. Although illustrated in FIG. 1 as an external device, the receiving device 106 may include an implantable device configured to communicate with the IMD 102 that may, for example, be a control device, another monitoring device, a pacemaker, an implantable defibrillator, a cardiac resynchronization therapy (CRT) device, and/or the like, and may be an implantable medical device known in the art or later developed, for providing therapy and/or diagnostic data about the patient and/or the IMD 102. In certain instances, the IMD 102 may be a pacemaker, an implantable cardioverter defibrillator (ICD) device, or a cardiac resynchronization therapy (CRT) device. In certain instances, the IMD 102 may include both defibrillation and pacing/CRT capabilities (e.g., a CRT-D device).

The system 100 may be used to implement coordinated patient measuring and/or monitoring, diagnosis, and/or therapy in accordance with embodiments of the disclosure. The system 100 may include, for example, one or more patient-internal medical devices, such as an IMD 102, and one or more patient-external medical devices, such as receiving device 106. The receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

The IMD 102 and the receiving device 106 may communicate through a wireless link. For example, the IMD 102 and the receiving device 106 may be coupled through a short-range radio link, such as Bluetooth, IEEE 802.11, and/or a proprietary wireless protocol. The communications link may facilitate uni-directional and/or bi-directional communication between the IMD 102 and the receiving device 106. Data and/or control signals may be transmitted between the IMD 102 and the receiving device 106 to coordinate the functions of the IMD 102 and/or the receiving device 106. Patient data may be downloaded from one or more of the IMD 102 and the receiving device 106 periodically or on command. The physician and/or the patient may communicate with the IMD 102 and the receiving device 106, for example, to acquire patient data or to initiate, terminate, or modify recording and/or therapy.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2A:
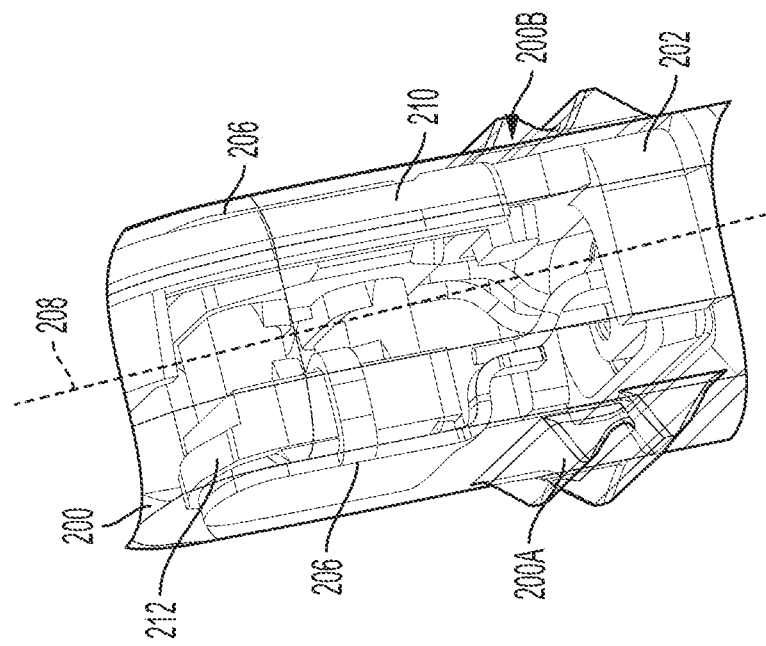
FIG. 2A is a front-facing view of a header and scaffold assembly.

FIG. 2A is a front-facing view of a header 200 and scaffold assembly 202. The scaffold assembly 202 may be an apparatus for supporting components of an implantable medical device (e.g., as shown in FIG. 1 and FIGS. 4A-B). The scaffold assembly 202 may be configured to support and separate a first electrode 204 and a second electrode 206 relative to a longitudinal axis 208 of the scaffold assembly 202.

Figure 2B:
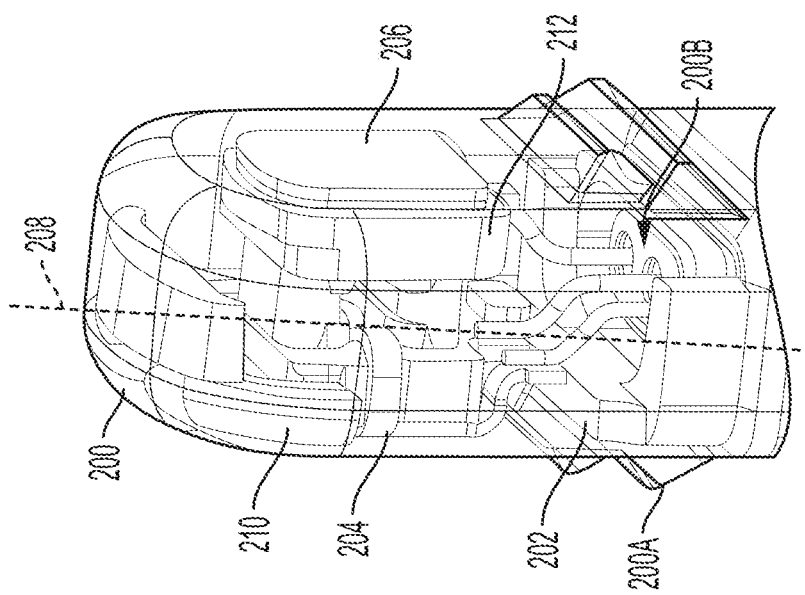
FIG. 2B is a back-facing view of the header and scaffold assembly shown in FIG. 2A.

In certain instances, the scaffold assembly 202 is configured to support the first electrode 204 along a first surface 210 of the scaffold assembly 202 and the second electrode 206 along a second surface 212 of the scaffold assembly 202 that opposes the first surface 210. The first surface 210 may be a frontward facing portion and the second surface 212 may be a rearward facing portion of the scaffold assembly 202 as shown in FIG. 2A and FIG. 2B. In other instances, the first surface 210 and the second surface 212 may be sides of the scaffold assembly 202. The scaffold assembly may be configured to arrange the first electrode 202 parallel to the second electrode 204.

FIG. 2B is a back-facing view of the header 200 and the scaffold assembly 202 shown in FIG. 2A. The header 200 includes an exterior surface 200A that encloses an interior region 200B. The header 202 may house various circuitry components within the interior region 200B such as the first electrode 204 and the second electrode 206. The exterior surface 200A may contact a patient's bodily tissue when an IMD, that includes the header 200, is subcutaneously implanted in an implantation location or pocket in the patient's chest or abdomen. The interior region 200B of the header 200 may provide a space and house the scaffold assembly 202 and circuit components positioned and supported by the scaffold assembly 202. In order to enable sensing of physiological parameters within the patient, the first electrode 204 and the second electrode 206 may be positioned to be flush with the interior region 200B of the header 200. In other instances, the first electrode 204 and the second electrode 206 may be positioned by the scaffold assembly 202 to form a portion of the exterior surface 200A of the header 202.

Figure 3B:
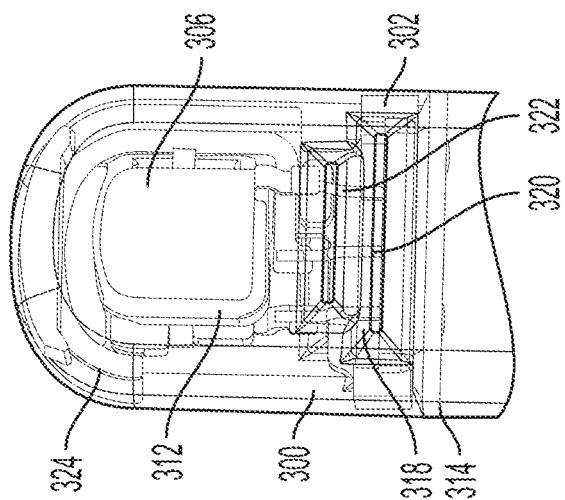
FIG. 3B is a back-facing view of the header and the scaffold assembly, and the core assembly shown in FIG. 3A.
Figure 3A:
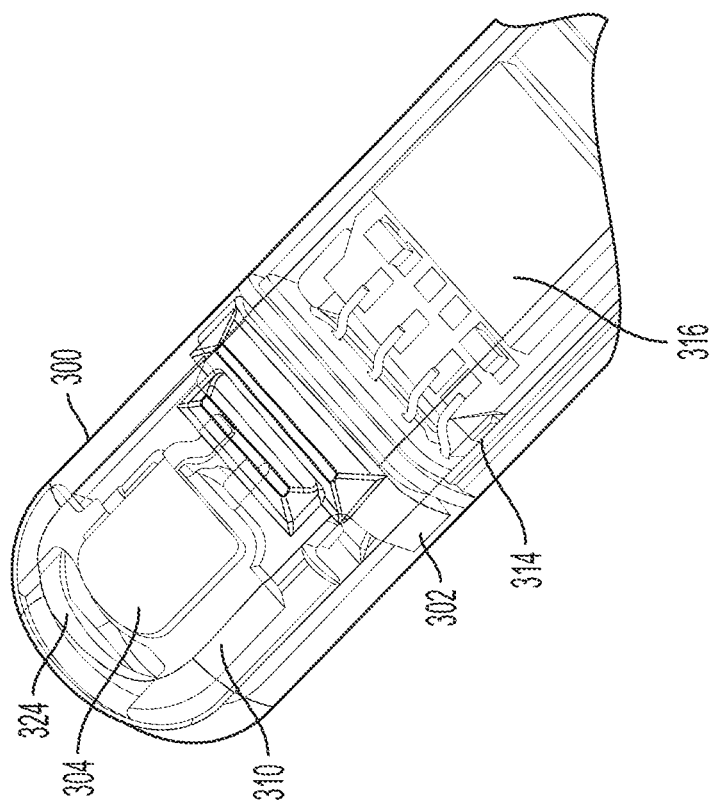
FIG. 3A is a front-facing view of a header, scaffold assembly, and core assembly.

FIG. 3A is a front-facing view of a header 300, scaffold assembly 302, and core assembly 314 and FIG. 3B is a back-facing view of the header 200 and the scaffold assembly 302, and the core assembly 314 shown in FIG. 3A. The scaffold assembly 302 includes a first surface 310 and a second surface 312. FIG. 3A also shows a portion of a core assembly 314. The header 300, scaffold assembly 302, and core assembly 314 may form portions of an IMD (e.g., as shown in FIG. 1 and FIGS. 4A-B). The scaffold assembly 304 may form a part of an apparatus for supporting components of the IMD. As such, an end portion and a portion of an intermediate section of the core assembly 314 is shown in FIG. 3A. Further, additional elements of the IMD may be included at the other end portion of the core assembly 314 (not shown). These elements may include a battery and an electrode.

The scaffold assembly 302 may be configured to support and position one or more circuit components. The scaffold assembly 302, for example, may be configured to interface with a portion of the IMD and configured to support the first electrode 304 along the first surface 310 of the scaffold assembly 302 and a second electrode 306 along the second surface 312 of the scaffold assembly 302. In certain instances, the second surface 312 of the scaffold assembly 302 opposes the first surface 310. In addition, the scaffold assembly 302 may be configured to arrange the first electrode 304 parallel to the second electrode 306.

In certain instances, the core assembly 314 includes integrated circuitry 316. The core assembly 314 may include one or more conduits that provide a feedthrough for at least one electrical connector or interconnect. As shown in FIG. 3B, interconnects 318, 320, 322 are provided and feed through the conduits to connect the first electrode 304 and the second electrode 306 to the integrated circuitry 316. In certain instances, the scaffold assembly 302 may also support an antenna 324. In these instances, one of the interconnects 318, 320, 322 may connect the antenna 324 to the integrated circuitry 316.

The functionality of the first electrode 304 and the second electrode 306 may be controlled by the integrated circuitry 316. For example, the integrated circuitry 316 may be configured to select between the first electrode 304 and the second electrode 306. In addition, the integrated circuitry 316 may be configured to measure sensing capability of the first electrode 304 and sensing capability of the second electrode 306. In certain instances, the integrated circuitry 316 may be configured to select between the first electrode 304 and the second electrode 306 in response to determining which of the first electrode 304 and the second electrode 306 has a greater of the sensing capability. The integrated circuitry 316 may be configured to measure impedance on a sensed signal of the first electrode 304 and an impedance on a sensed signal of the second electrode 306 to determine the sensing capability of the first electrode 304 and the sensing capability of the second electrode 306.

The scaffold assembly 302 supporting and arranging the first electrode 304 and the second electrode 306 may reduce sensing noise when impedance is measured (as compared to a device having a single electrode in a header). In addition, the integrated circuitry 316 being configured to select between the first electrode 304 and the second electrode 306 may increasing sensing capabilities and signal capture as compared to a device having a single electrode within a header. As noted above The scaffold assembly 304 may form a part of an apparatus for supporting components of an IMD. When implanted, the IMD may turn or flip which may affect sensing capability of the IMD. The integrated circuitry 316 being configured to select between the first electrode 304 and the second electrode 306 allows for selecting of whichever of the first electrode 304 and the second electrode 306 has the stronger signal for sensing.

During the impedance measurement, the integrated circuitry 316 may be configured to drive a signal to one of the first electrode 304 and the second electrode 306 while sensing on the other of the first electrode 304 and the second electrode 306. In these instances, the integrated circuitry 316 may drive the signals to the first electrode 304 and the second electrode 306 in a loop to isolate the sensed signals.

In certain instances, functionality of the circuitry components supported and arranged by the scaffold assembly 302 may depend on the arrangement or positioning of the circuitry components. More specifically, unintended or uncontrolled movement of one or more circuitry components, such as the first electrode 304 and the second electrode 306, may disconnect from integrated circuitry 316. In addition, the scaffold assembly 302 facilitates arranging the first electrode 304 and the second electrode 306 to ensure that the first electrode 304 and the second electrode 306 are arranged on opposite sides of the IMD to facilitate sensing.

In addition, the functionality of antenna 324 may also controlled by integrated circuitry 316 housed within the core assembly 314. The scaffold assembly 302 may center the antenna 324 between the first electrode 304 and the second electrode 306. In this manner, the scaffold assembly 302 may facilitate performance of the antenna 324 and avoid RF interference by keeping the antenna 324 from muscle tissue and closer to the skin side (e.g., exterior side of a patient's body) of the header 300 so there is less body tissue to transmit through.

The illustrative components shown in FIG. 3A and FIG. 3B are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in FIG. 4A and FIG. 4B (discussed in further detail below) may be, in embodiments, integrated with various other components depicted therein (and/or components not illustrated), all of which are considered to be within the ambit of the disclosed subject matter.

FIG. 4A is a front-facing view of an IMD 400 and FIG. 4B is a back-facing view of the IMD. The IMD may be, or may be similar to, the IMD 102 depicted in FIG. 1. The scaffold assembly 402 includes a first surface 410 and a second surface 412. The scaffold assembly 404 may form a part of an apparatus for supporting components of the IMD. The IMD also includes a core assembly 414, which may house integrated circuitry (not shown) internal to the core assembly 414. The core assembly 414 also includes a battery 426 and a third electrode 428.

The scaffold assembly 402 may be configured to support and position one or more circuit components. The scaffold assembly 402 is configured to interface with a portion of the core assembly 414 (e.g., as shown in FIGS. 3A-B). The scaffold assembly 402 may be configured to support and separate a first electrode 404 and a second electrode 406 relative to a longitudinal axis of the scaffold assembly 402. The scaffold assembly 402 may be configured to support the first electrode 404 along the first surface 410 of the scaffold assembly 402 and a second electrode 406 along the second surface 412 of the scaffold assembly 402. In certain instances, the second surface 412 of the scaffold assembly 402 opposes the first surface 410. In addition, the scaffold assembly 402 may be configured to arrange the first electrode 404 parallel to the second electrode 406. In addition, the first electrode 404 may include a first area and the second electrode 406 includes a second area that is substantially equal to the first area.

The functionality of the first electrode 404, the second electrode 406, and the third electrode 428 may be controlled by the integrated circuitry. In certain instances, the integrated circuitry may be configured to select between the first electrode 404 and the second electrode 406. In addition, the integrated circuitry may be configured to measure sensing capability of the first electrode 404 and sensing capability of the second electrode 406. In certain instances, the integrated circuitry may be configured to select between the first electrode 404 and the second electrode 406 in response to determining which of the first electrode 404 and the second electrode 406 has a greater of the sensing capability.

The integrated circuitry may be configured to measure impedance on a sensed signal of the first electrode 404 and an impedance on a sensed signal of the second electrode 406 to determine the sensing capability of the first electrode 404 and the sensing capability of the second electrode 406. In certain instances, the integrated circuitry is configured to drive the third electrode 428 and one of the first electrode 404 and the second electrode 406 and to sense another of the first electrode 404 and the second electrode 406. In addition, the integrated circuitry includes a Kelvin connection to the first electrode 404 and the second electrode 406.

In certain instances, the core assembly 414 may include an accelerometer to determine whether or not the IMD has turned or flipped. The accelerometer may determine periods of electrode inactivity to determine a stable signal and select between the first electrode 404 and the second electrode 406.

The scaffold assembly 402 supporting and arranging the first electrode 404 and the second electrode 406 may reduce sensing noise when impedance is measured (as compared to a device having a single electrode in a header). In addition, the integrated circuitry being configured to select between the first electrode 404 and the second electrode 406 may increasing sensing capabilities and signal capture as compared to a device having a single electrode within a header. As noted above, the scaffold assembly 404 may form a part of an apparatus for supporting components of an IMD. When implanted, the IMD may turn or flip which may affect sensing capability of the IMD. The integrated circuitry being configured to select between the first electrode 404 and the second electrode 406 allows for selecting of whichever of the first electrode 404 and the second electrode 406 has the stronger signal for sensing.

In certain instances, the scaffold assembly 402 may also support an antenna 424. In addition, interconnects may connect the antenna 424 to the integrated circuitry. The antenna 424 may be arranged along a top surface of the scaffold assembly 402. In addition, the functionality of antenna 424 may also controlled by integrated circuitry housed within the core assembly 414. The scaffold assembly 302 may center the antenna 424 between the first electrode 404 and the second electrode 406. In this manner, the scaffold assembly 402 may facilitate performance of the antenna 424 and avoid RF interference by keeping the antenna 324 from muscle tissue and closer to the skin side (e.g., exterior side of a patient's body) of the header 400 so there is less body tissue to transmit through.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An apparatus for supporting components of an implantable medical device, the apparatus comprising:
    a first electrode and a second electrode;
    a scaffold assembly configured to interface with a portion of the implantable medical device and configured to support the first electrode along a first surface of the scaffold assembly and the second electrode along a second surface of the scaffold assembly that opposes the first surface; and
    an integrated circuitry configured to:
        drive a signal to the first electrode and a signal to the second electrode;
        measure an impedance on the driven signal of the first electrode and an impedance on the driven signal of the second electrode to determine a sensing capability of the first electrode and a sensing capability of the second electrode;
        drive one of the first electrode and the second electrode in a loop; and
        sense another of the first electrode and the second electrode.

2. The apparatus of claim 1, wherein the scaffold assembly is configured to arrange the first electrode parallel to the second electrode.

3. The apparatus of claim 2, wherein the scaffold assembly includes a frontward facing portion and a rearward facing portion, and the first electrode is arranged on the frontward facing portion and the second electrode is arranged on the rearward facing portion.

4. The apparatus of claim 1, wherein the implantable medical device comprises a header and a core assembly, the core assembly including the integrated circuitry configured to select between the first electrode and the second electrode.

5. The apparatus of claim 4, wherein the integrated circuitry is configured to:
   measure the sensing capability of the first electrode;
   measure the sensing capability of the second electrode; and
   select between the first electrode and the second electrode in response to determining a greater of the sensing capability of the first electrode and the sensing capability of the second electrode.

6. The apparatus of claim 4, wherein the first electrode and the second electrode are arranged at a proximal end of the core assembly and the apparatus further comprises a third electrode arranged at a distal end of the core assembly.

7. The apparatus of claim 6, wherein the integrated circuitry is configured to:
   drive the third electrode and one of the first electrode and the second electrode; and
   sense another of the first electrode and the second electrode.

8. The apparatus of claim 4, wherein the scaffold assembly is arranged within the header and the scaffold assembly is configured to support and position the first electrode with a first surface of an interior portion of the header and position the second electrode with a second surface of the interior portion of the header.

9. The apparatus of claim 1, further comprising an antenna arranged on the scaffold assembly and between the first electrode and the second electrode.

10. The apparatus of claim 4, wherein the first electrode includes a first area and the second electrode includes a second area, the first area being equal to the second area.

11. An apparatus comprising:
   a medical device configured to be implanted within a body of a patient comprising:
      a core assembly having a proximal end and a distal end;
      a header coupled to the proximal end of the core assembly;
      a first electrode and a second electrode arranged within the header;
      a third electrode arranged at the distal end of the core assembly;
      an integrated circuitry arranged within the core assembly; and
      a scaffold assembly arranged within the header and configured to support and separate the first electrode and the second electrode relative to a longitudinal axis of the scaffold assembly;
   wherein the integrated circuitry is configured to:
      drive a signal to the first electrode and a signal to the second electrode;
      measure an impedance on the driven signal of the first electrode and an impedance on the driven signal of the second electrode to determine a sensing capability of the first electrode and a sensing capability of the second electrode;
      drive one of the first electrode and the second electrode in a loop; and
      sense another of the first electrode and the second electrode.

12. The apparatus of claim 11, wherein the scaffold assembly is configured to interface with a portion of the core assembly and configured to support the first electrode along a first surface of the scaffold assembly and the second electrode along a second surface of the scaffold assembly that opposes the first surface.

13. The apparatus of claim 11, wherein the integrated circuitry is further configured to:
   measure the sensing capability of the first electrode;
   measure the sensing capability of the second electrode; and
   select between the first electrode and the second electrode in response to determining a greater of the sensing capability of the first electrode and the sensing capability of the second electrode.

14. The apparatus of claim 13, wherein the integrated circuitry is further configured to:
   drive the third electrode and one of the first electrode and the second electrode; and
   sense another of the first electrode and the second electrode.

15. The apparatus of claim 13, wherein the scaffold assembly is arranged within the header and the scaffold assembly is configured to support and position the first electrode with a first surface of an interior portion of the header and position the second electrode with a second surface of the interior portion of the header.

* * * * *